United States Patent
Sun et al.

(10) Patent No.: US 9,284,281 B2
(45) Date of Patent: Mar. 15, 2016

(54) INDICATION OF NAPHTHO[2,3-F]QUINOXALINE-7,12-DIONE COMPOUND IN ALLEVIATING PAIN

(71) Applicant: NATIONAL CENTRAL UNIVERSITY, Taoyuan County (TW)

(72) Inventors: Wei-Hsin Sun, Taoyuan County (TW); Shir-Ly Huang, Taoyuan County (TW); Hsu-Shan Hunag, Taoyuan County (TW)

(73) Assignee: NATIONAL CENTRAL UNIVERSITY, Jhongli (TW)

( * ) Notice: Subject to any disclaimer, the term of this patent is extended or adjusted under 35 U.S.C. 154(b) by 37 days.

(21) Appl. No.: 14/487,876

(22) Filed: Sep. 16, 2014

(65) Prior Publication Data

US 2015/0259302 A1    Sep. 17, 2015

(30) Foreign Application Priority Data

Mar. 11, 2014 (TW) .............................. 103108518 A

(51) Int. Cl.
*A61K 31/498* (2006.01)
*C07D 241/44* (2006.01)
*C07D 241/42* (2006.01)

(52) U.S. Cl.
CPC ............ *C07D 241/44* (2013.01); *C07D 241/42* (2013.01)

(58) Field of Classification Search
CPC .................................................... A61K 31/498
USPC ........................................................... 514/250
See application file for complete search history.

(56) References Cited

U.S. PATENT DOCUMENTS 8,222,287 B2 *    7/2012    Huang ................. C07D 235/08
                                                        514/393

FOREIGN PATENT DOCUMENTS

| TW | I245036 | 12/2005 |
| TW | I406662 | 10/2008 |
| TW | 201249792 | 12/2012 |
| TW | I378792 | 12/2012 |
| TW | I399369 | 6/2013 |
| TW | I402066 | 7/2013 |

OTHER PUBLICATIONS

Linhart et al., the Inflammatory Mediators Serotonin, Prostaglandin E2 and Bradykinin Evoke Calcium Influx in Rat Sensory Neurons; Neuroscience, 2003; 118(1):69-74.

* cited by examiner

*Primary Examiner* — Scarlett Goon
*Assistant Examiner* — Sonya Wright
(74) *Attorney, Agent, or Firm* — Volpe and Koenig, P.C.

(57) ABSTRACT

Disclosed are naphtho[2,3-f]quinoxaline compounds and pharmaceutical composition thereof. The compounds of the invention have been demonstrated as having analgesic effects and therefore may be applicable for use as a novel agent in relieving acute or chronic pain.

4 Claims, 8 Drawing Sheets

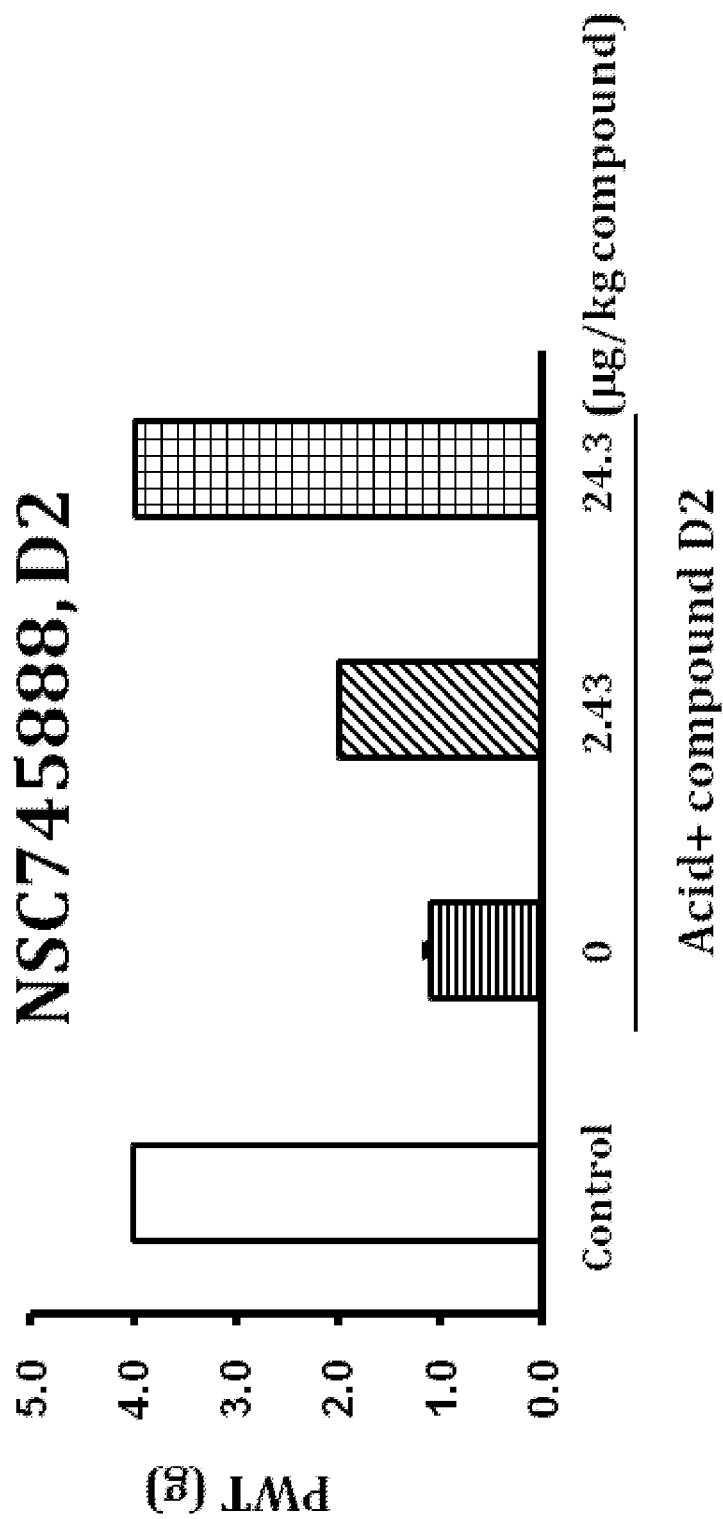

INDICATION OF NAPHTHO[2,3-F]QUINOXALINE-7,12-DIONE COMPOUND IN ALLEVIATING PAIN

CROSS REFERENCE TO RELATED APPLICATIONS

This application claims benefit under 35 U.S.C. §119 of Taiwan Application No. 103108518, filed Mar. 11, 2014, the contents of which are incorporated by reference as if fully set forth.

FIELD OF THE INVENTION

The present invention relates to naphtho[2,3-f]quinoxaline compounds and pharmaceutical compositions thereof, which demonstrates analgesic effects. In particular, the present invention relates to an application in the pharmaceutical field.

BACKGROUND OF THE INVENTION

Naphtho[2,3-f]quinoxaline-7,12-dione compounds such as Formula I and Formula II are kinds of anthraquinone derivatives containing a heterocyclic group, where the synthesis and the effectiveness of the compounds to inhibit cancer cell activity through stabilizing G-quadruplex construction to suppress telomerase activity are both disclosed in Taiwan Patent Application No. 097112087.

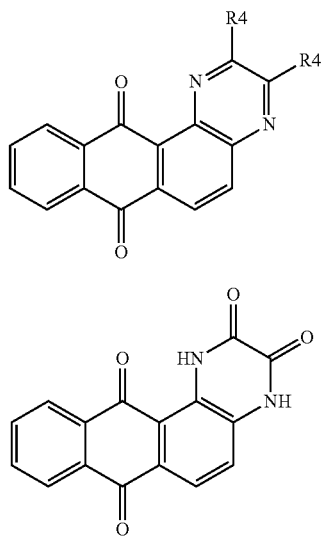

The R4 is selected from hydrogen or methyl.

The known tricyclic anthraquinone derivatives, for example, the 2,3-dihydroimidazo[1,2-c]quinazoline compounds disclosed in Taiwan Patent No. 1378792; Taiwan Patent No. I402066; Taiwan Publication No. 201249792 and Taiwan Publication No. 200840582 can be used for the treatment of the excessive growth of cancer cells and the formation of the vessels accompanying the cells. In addition to the effects mentioned above, the compounds disclosed in Taiwan Patent No. I245036 not only inhibit tumor cell lines, but also have anti-allergic and anti-inflammatory properties as well. However, existing literature does not disclose whether anthraquinone derivatives can ease pain or can be applied to pharmaceutical use as an analgesic.

In order to overcome the drawbacks in the prior art, an indication of naphtho[2,3-f]quinoxaline-7,12-dione compound for alleviating pain is disclosed. The particular design in the present invention not only solves the problems described above, but is also easy to implement. Thus, the present invention has substantial utility for the industry.

SUMMARY OF THE INVENTION

To overcome the drawbacks in the prior art, the present invention investigated the effectiveness of alleviating pain by conducting animal experiments. Particularly, the present invention refers to a pharmaceutical application of naphtho[2,3-f]quinoxaline compounds.

In accordance with an aspect of the present invention, the pharmaceutical application of alleviating pain includes methods and compositions, which can be applied to any acute pain or chronic pain in an organism caused by inflammation, injury, or neuropathy.

In accordance with another aspect of the present invention, a method for alleviating pain is disclosed. The method includes a step of administering to a subject suffering the pain a pharmaceutical compound or a pharmaceutical composition, where the compound and the composition includes a naphtho[2,3-f]quinoxaline compound represented by Formula I and Formula II:

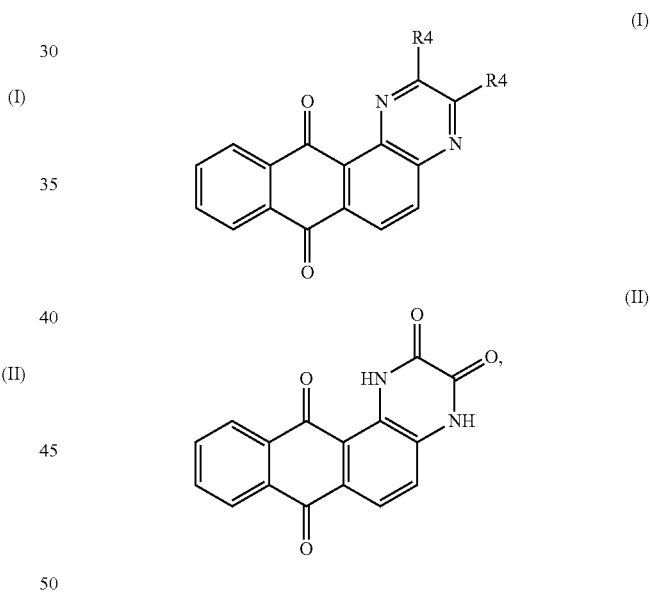

and R4 is one of hydrogen and methyl.

The above objectives and advantages of the present invention will become more readily apparent to those ordinarily skilled in the art after reviewing the following detailed descriptions and accompanying drawings, in which:

BRIEF DESCRIPTION OF THE DRAWINGS

FIG. 1C shows the therapeutic effect of the compound D2 for alleviating nociceptive pain.

DETAILED DESCRIPTION OF THE PREFERRED EMBODIMENTS

Figure 1A:
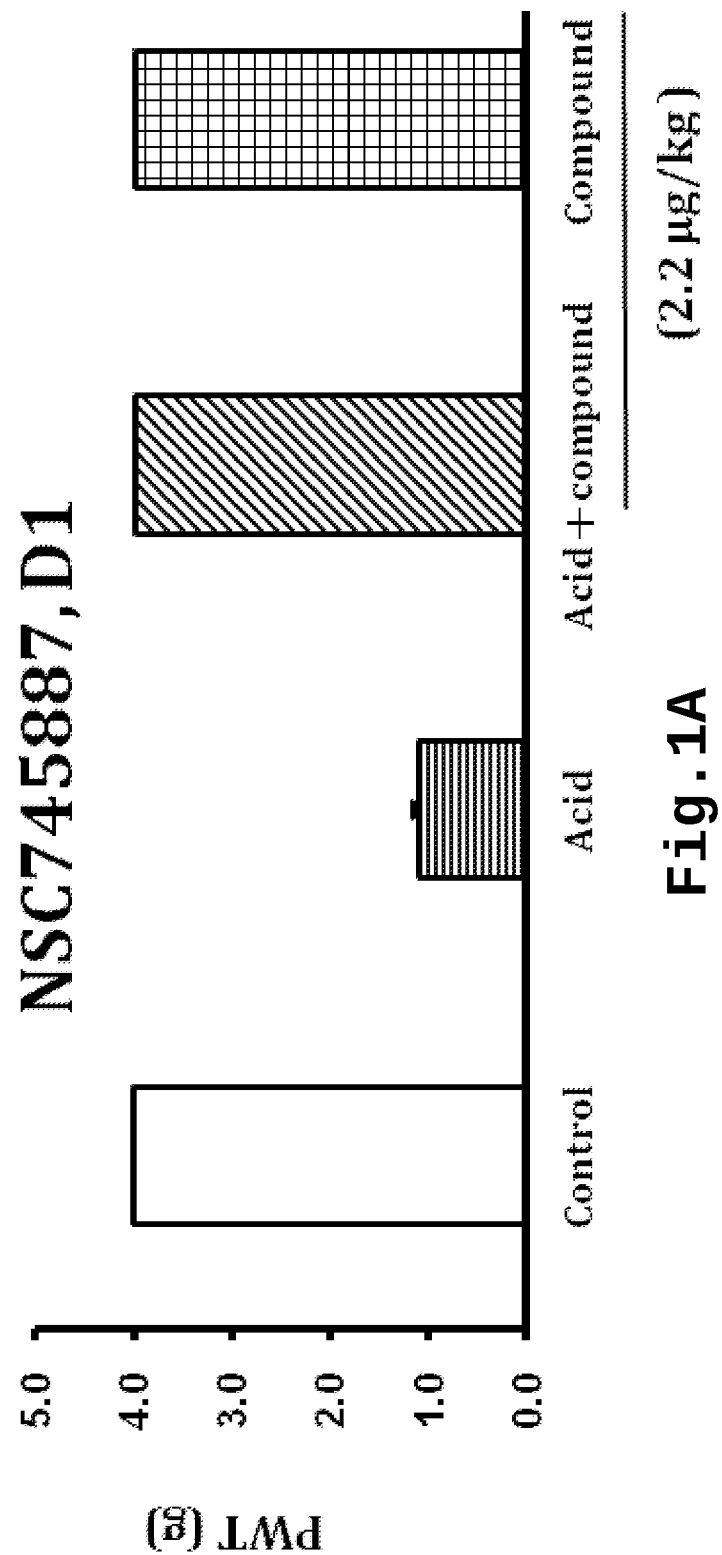
FIG. 1A shows the therapeutic effect of the compound D1 for alleviating nociceptive pain.

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

The synthetic strategy of naphtho[2,3-f]quinoxaline compounds that the present invention provides is shown below: 1,2-Diaminoanthraquinone is dissolved in N,N-dimethylformamide (DMF) as a raw material to synthesize related products as required. When the raw material reacts with methyl vinyl ketone, 2,3-dimethylnaphtho[2,3-f]quinoxaline-7,12-dione (NSC745886, C3) can be obtained, where the $2^{nd}$ and $3^{rd}$ positions of the compound are methyls. When the raw material reacts with glyoxal, naphtho[2,3-f]quinoxaline-7,12-dione (NSC745887, D1) can be obtained. Furthermore, naphtho[2,3-f]quinoxaline-2,3,7,12(1H,4H)-tetraone (NSC745888, D2), as shown in Formula II, can be obtained by the reaction of the raw material with oxalic acid.

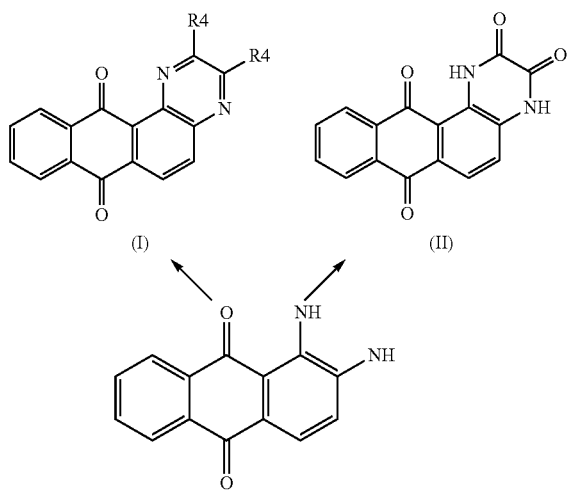

R4 is one of hydrogen and methyl.

Pain is defined as unpleasant sensory or emotional experience resulting from the damage of body tissue according to the International Association for the Study of Pain (IASP), which is characterized as two types: acute pain or chronic pain. Pain decreases normally within 1 to 3 months after the removal of injured tissue and the application of the proper medicine, and is classified as acute pain, such as the pain caused by appendicitis. On the contrary, if the duration of the pain is longer than that of expectant recovery or the pain itself becomes a sickness, the pain is classified as chronic pain.

Chronic pain, such as long-term pain contributed to by cancer, usually continues for more than six months. Therefore, patients suffering from this pain need suitable therapies to alleviate their symptoms.

Clinically speaking, pain in organisms may be inflammatory pain which results from tissue inflammation, nociceptive pain which is the pain caused by direct noxious stimulation of the receptors on pain-related nerves, neuropathic pain resulting from dysfunction or damage of the central or peripheral nervous system caused by injury or diseases.

Pain is characterized by the hypersensitivity of the injured area and the surrounding normal tissue. Morphine-like drugs are usually effective on pain for a limited period; however, neuropathic pain can be long-lasting even after the recovery from the events that caused it, e.g. "phantom pain" after amputation. Chronic pain syndrome can be induced by any form of injury, including surgery, oppressive injury, trauma, pathogenic factors, poison, abnormal inflammation and metabolic dysfunction, such as diabetes and ischemia.

Unfortunately, the adaptive therapeutic drugs to alleviate chronic neuropathic pain such as anti-melancholia tricyclic medicine, anti-invasion drugs and local anesthetics only ease the pain temporally or achieve different levels of relief. Moreover, the current therapies typically have severe side effects, for example, change of cognition, sedation, nausea, or narcotic addiction. Therefore, a novel method to alleviate chronic pain over the long term is still needed.

The term "organism" as utilized herein includes humans, dogs, cats, cows, pigs, sheep, horses and other mammals. The term "pain" as utilized herein generally includes chronic pain, acute pain and pain which is based on inflammation or neuropathy in different tissues. The term "administration" as utilized herein means alleviating the pain of an organism by giving a compound or a pharmaceutical composition to the organism. The administration includes, but is not limited to, oral administration and injection. In further Embodiments, the naphtho[2,3-f]quinoxaline compounds are administered by intraplantar, intrathecal, or intraperitoneal injection.

The term "inflammation" as utilized herein, can be characterized into two types: acute inflammation and chronic inflammation. When tissue is injured, bleeding or infected by pathogens, a physiological response will be aroused due to the release of proinflammatory cytokine, such as histamine, prostaglandin, interleukin, TNF-α, monocyte chemoattractant protein-1 (MCP-1), and interferon-γ (IFN-γ). Prolonged inflammation may lead to a variety of diseases, for example, rheumatoid arthritis or cancer.

The term "alleviate pain" as utilized herein, generally refers to the relief of any type of pain, wherein the pain includes, but is not limited to, neuropathic pain such as the pain caused by diabetes, visceral pain, post-operative pain, pain caused by cancer or treatments of cancer, and inflammatory pain caused by arthritis or irritable bowel syndrome, headache and muscle pain.

Nociceptive Pain—the Animal Model of Acute Pain Induced Using an Acid Solution to Evaluate the Analgesic Effect of the Compound Naphtho[2,3-f]quinoxaline-7,12-dione compound was intraplantarly injected into the right hind paws of 8 to 12-week-old CD-1 mice. 5 minutes after the injection, 25 μL of pH 5.0 acid solution was intraplantarly injected into each of the mice. About 60 minutes later, the mice were directly tested with the hypersensitivity to mechanical stimuli using von Frey filaments (Touch-Test North Coast Medical, Inc., Margan Hill, Calif.). The control group was conducted under the same conditions except it was treated with a compound-free saline. The results are shown in FIG. 1, where the injection of 25 µL of the pH 5.0 acid solution induced mechanical hyperalgesia in the right hind paw of the mice, and the paw withdrawal threshold (PWT) of these mice was 1.1±0.065 g. By injecting 2.2 µg/kg of the naphtho[2,3-f]quinoxaline-7, 12-dione (NSC745887, D1) compound intraplantarly into the right hind paws of the mice, the paw withdrawal threshold of those mice recovered to 4.0±0 g (PWT of control group mice was 4.0±0 g). Therefore, 2.2 µg/kg of the naphtho[2,3-f]quinoxaline-7,12-dione (NSC745887, D1) compound effectively inhibited the acute pain caused by the acid solution. The sole injection of the compound without the acid solution into the mice did not induce pain; the paw withdrawal threshold of the mice was still 4.0±0 g, which indicates that the compound did not arouse a pain response.

Figure 1B:
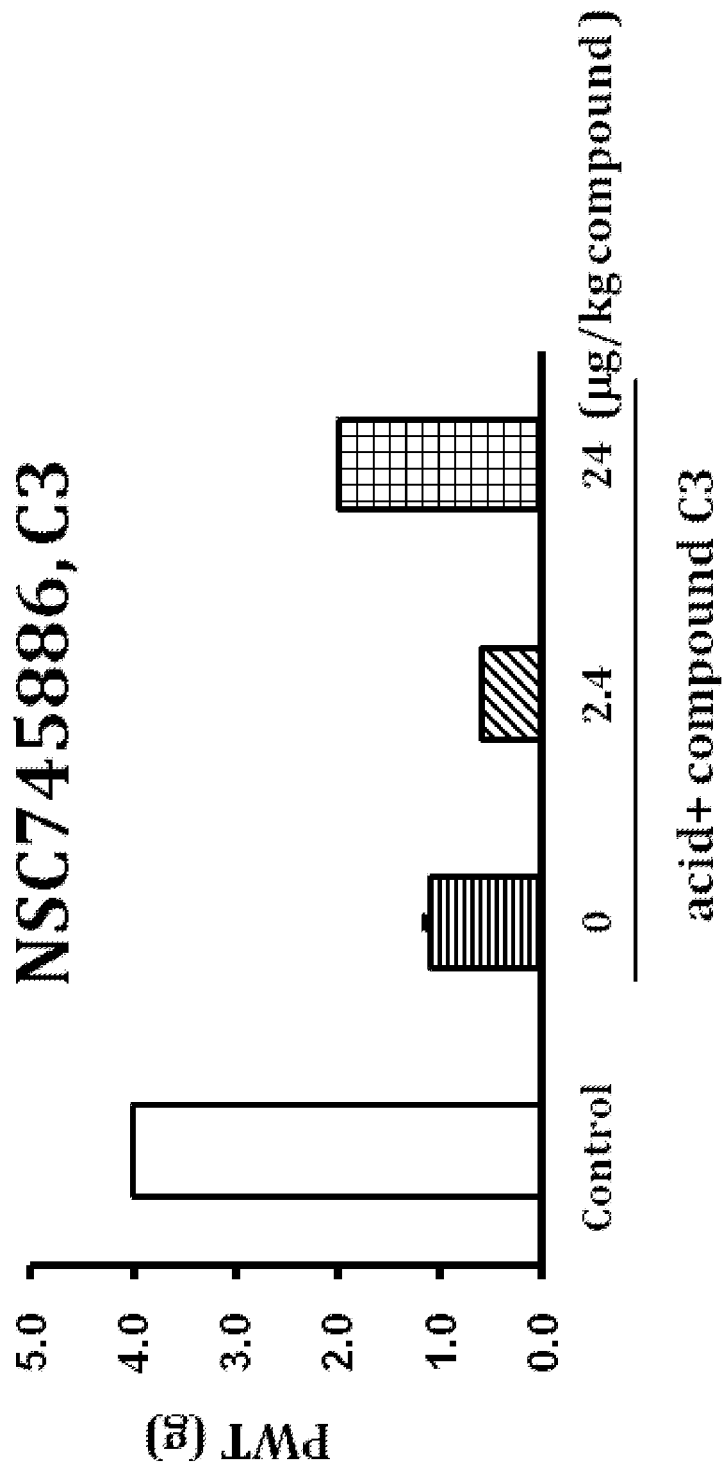
FIG. 1B shows the therapeutic effect of the compound C3 for alleviating nociceptive pain.

Some of the mice were intraplantarly injected with 2.4 or 24 µg/kg of the compound C3 (NSC745886) into the right hind paws, which was followed by the injection of the pH 5.0 acid solution inducing mechanical hyperalgesia in the same manner. As shown in FIG. 1B, when the dosage reached 24 µg/kg, the PWT of these mice recovered to 2.0±0 g (PWT of control group mice was 4.0±0 g), showing that 24 µg/kg of the compound C3 (NSC745886) can reduce the acute pain induced by acid solution.

Some of the mice were intraplantarly injected with 2.43 or 24.3 µg/kg of the compound D2 (NSC745888) into the right hind paws, which was followed by the injection of the pH 5.0 acid solution inducing mechanical hyperalgesia in the same manner. According to the FIG. 1C, when the dosage reached 24.3 µg/kg, the PWT of these mice recovered to 4.0±0 g (PWT of control group mice was 4.0±0 g), showing that 24.3 µg/kg of the compound D2 (NSC745888) can alleviate the acute pain induced by acid solution.

The effective dosage of the compound D1 (2.2 µg/kg) is less than that of the compound C3 (24 µg/kg) and the compound D2 (24.3 µg/kg). Furthermore, while using the same dosage of the compound D2 and the compound C3 (24 µg/kg), the compound D2 can inhibit the pain completely (the PWT of the mice administered the compound D2 recovered to 4.0±0 g). That is, the D2 compound is more effective than the C3 compound.

Neuropathic Pain—the Animal Model of Chronic Neuropathic Pain Induced by Chronic Constriction Injury (CCI) of the Sciatic Nerve to Evaluate the Analgesic Effect of the Compound The assessment of the effectiveness of the compound for alleviating neuropathic pain used the animal model of chronic constriction injury (CCI) of the sciatic nerve, which was established by Bennett and Xie (1988). After the surgery, the mice developed long-lasting hypersensitivity to mechanical stimuli (chronic mechanical hyperalgesia), even being lightly touched. The mechanical hyperalgesia test was used to evaluate the analgesic effect of the compound.

The mice, after a week following the surgery, were intraplantarly injected with a series of different dosages of the naphtho[2,3-f]quinoxaline-7,12-dione compound, 0.22, 2.2, 22 µg/kg, or the mice were injected with 2.2 µg/kg of compound intrathecally, or with 43 µg/kg of the compound intraperitoneally. The hypersensitivity to mechanical stimuli was measured using von Frey filaments at 60 minutes after the injection. The mice injected with saline following surgery were the control group and the other mice injected with gabapentin following surgery were the positive control group.

Figure 2A:
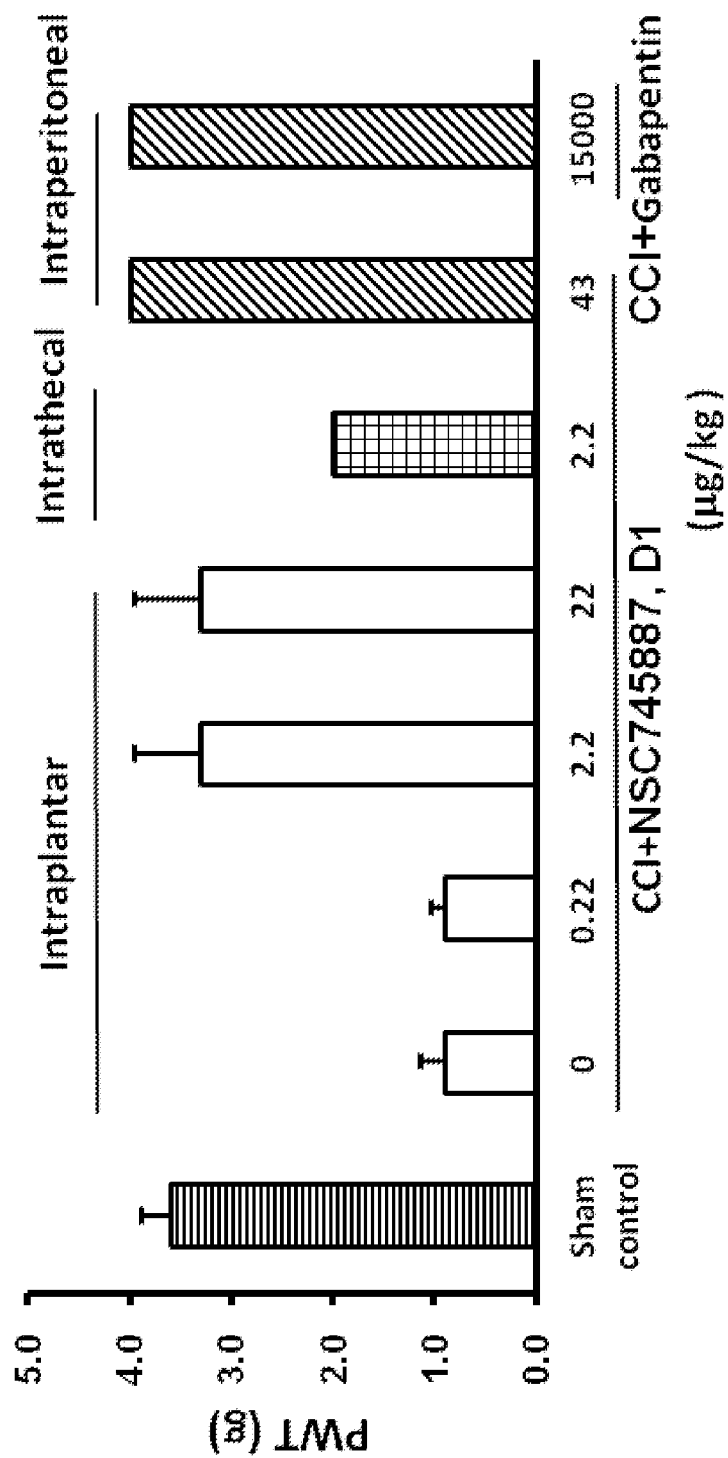
FIG. 2A shows the therapeutic effect of the compound D1 for alleviating chronic neuropathic pain using different routes of administration.

As shown in FIG. 2A, the paw withdrawal threshold (PWT) of the mice after a week following the surgery decreased to 0.9±0.23 g but that of the mice that were intraplantarly administered with 2.2 µg/kg of the D1 (NSC745887) compound recovered to 3.3±0.67 g (that of the control group following surgery was 3.6±0.29 g). The result indicates that the compound effectively alleviates the chronic mechanical hyperalgesia caused by CCI of the sciatic nerve. When the dosage was increased to 22 µg/kg, the paw withdrawal threshold remained 3.3±0.67 g. The same dosage of 2.2 µg/kg was injected intrathecally into mice and reduced the mechanical hyperalgesia (PWT was 2.0 g), though it did not completely inhibit hyperalgesia.

The intraperitoneal injection of 43 µg/kg of the compound also completely inhibited mechanical hyperalgesia induced by CCI of the sciatic nerve. By contrast, the current therapeutic medicine for alleviating neuropathic pain is gabapentin, and at least 15,000 µg/kg is required for intraperitoneal injection to inhibit the chronic mechanical hyperalgesia caused by CCI of the sciatic nerve. The effective dosage of naphtho[2,3-f]quinoxaline compounds for inhibiting neuropathic pain is substantially less than that of gabapentin. In addition, it was also proven that the effective dosage required for intraplantar injection was lower than that for intrathecal or intraperitoneal injection.

Figure 2B:
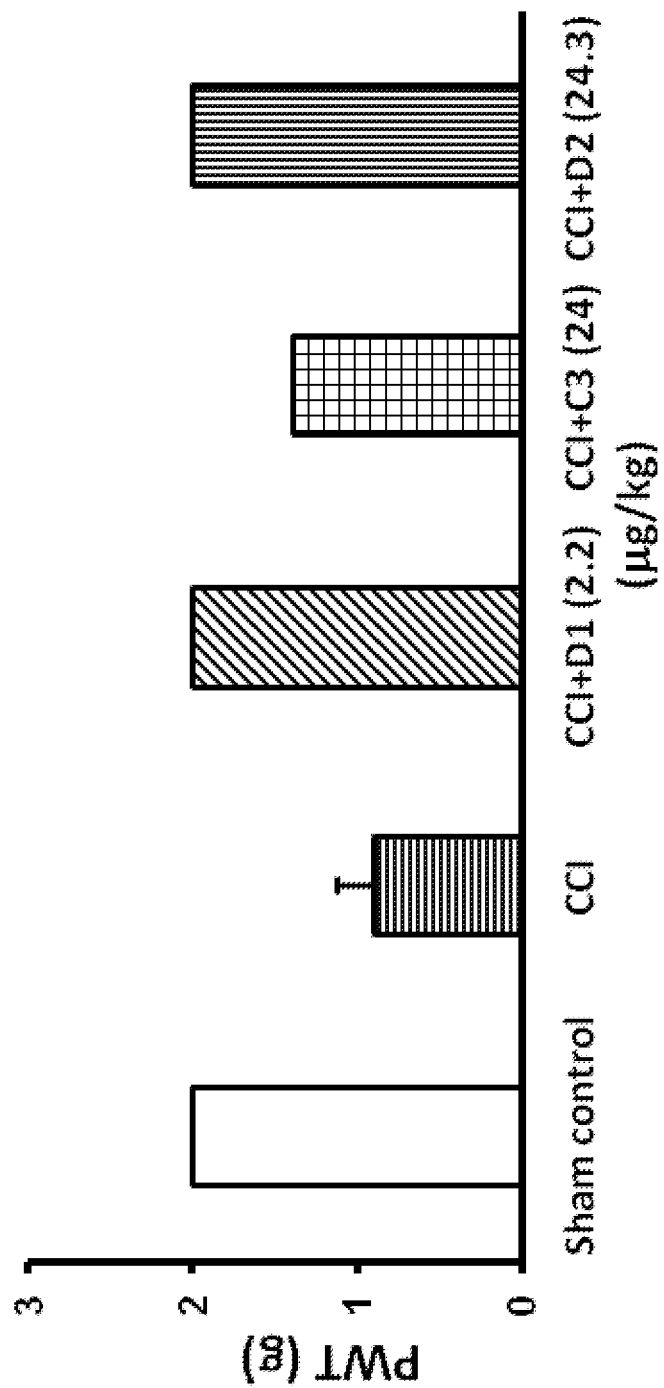
FIG. 2B shows the effect of inhibition of the compound D1, C3 and D2 and the therapeutic effect of the compounds D1, C3 and D2 for alleviating chronic neuropathic pain using intraplantar administration.

As shown in FIG. 2B, the paw withdrawal threshold (PWT) of the mice after a week following the surgery decreased to 0.9±0.23 g but that of the mice that were intraplantarly administered with 2.2 µg/kg of the compound D1 (NSC745887) or 24.3 µg/kg of the D2 (NSC745888) compound recovered to 2.0±0 g, which was the same as that of the control group following surgery. Injecting 24 µg/kg of the C3 (NSC745886) compound into the mice may ease the pain caused by CCI of the sciatic nerve, however, it did not completely alleviate the pain (the PWT of the mice recovered to 1.4 g). This result indicates that the effective dosage of the compound D1 is less than that of D2 and C3.

Figure 3:
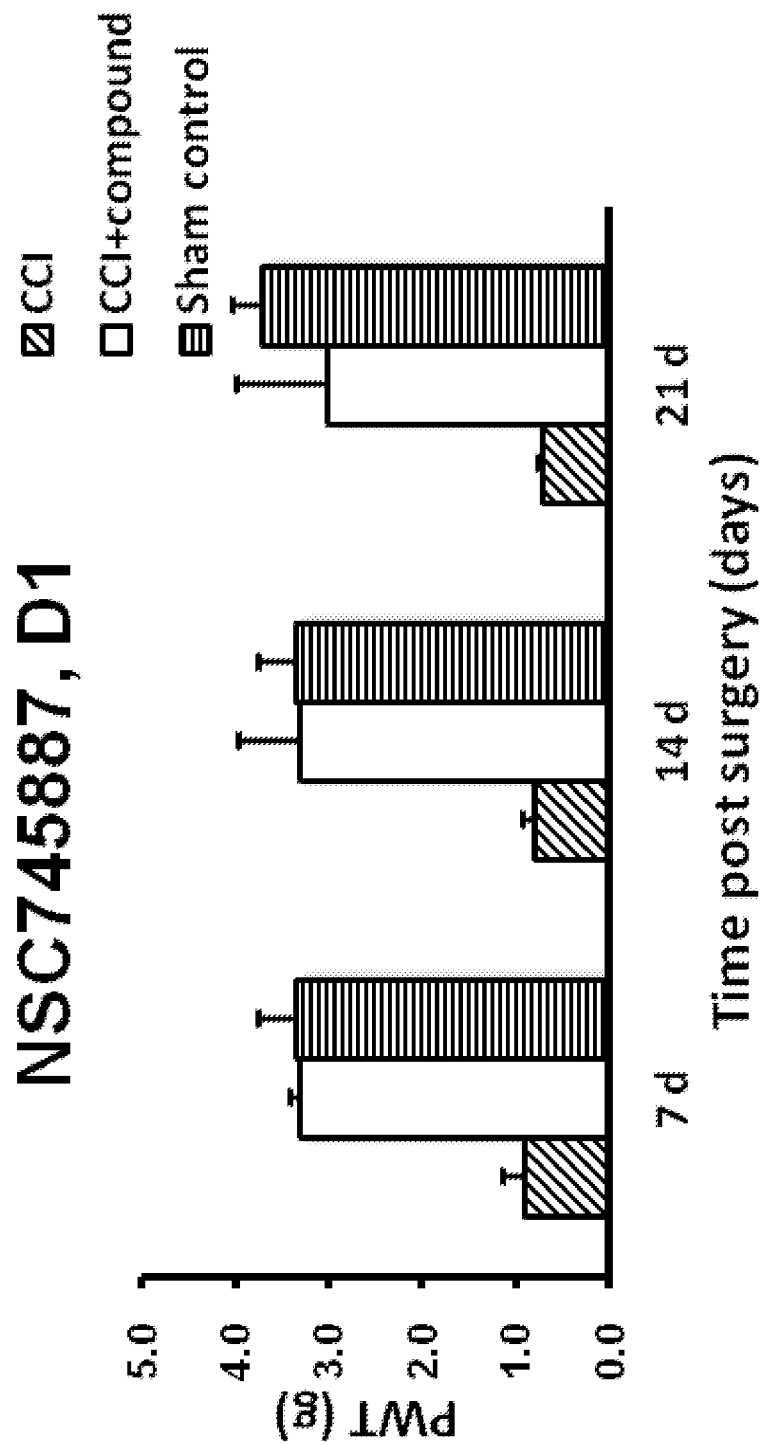
FIG. 3 shows the therapeutic effect of the compound D1 for alleviating chronic neuropathic pain under administration once every week for three weeks.

As shown in FIG. 3, the mice that had CCI of the sciatic nerve were intraplantarly injected with 2.2 µg/kg of the naphtho[2,3-f]quinoxaline-7,12-dione compound once every week for three weeks. The PWT in the first week was 3.3±0.67 g, the second week was 3.3±0.67 g and the third week was 3.0±0.1 g, and the data shows that there was no obvious indication that the mice developed tolerance to the compound.

Inflammatory Pain—the Chronic Inflammatory Pain Induced by Complete Freund's Adjuvant (CFA)

When 50% CFA was intraplantarly injected into the mouse, paw edema and chronic mechanical hyperalgesia were developed in the tested mice. Different dosages of the naphtho[2,3-f]quinoxaline-7,12-dione compound, 0.22, 2.2, 22 µg/kg were intraplantarly injected into mouse hindpaw, followed by 50% CFA injection. At 60 minutes after the CFA injection, the hypersensitivity of the mice to mechanical stimuli was measured using von Frey filaments.

Figure 4A:
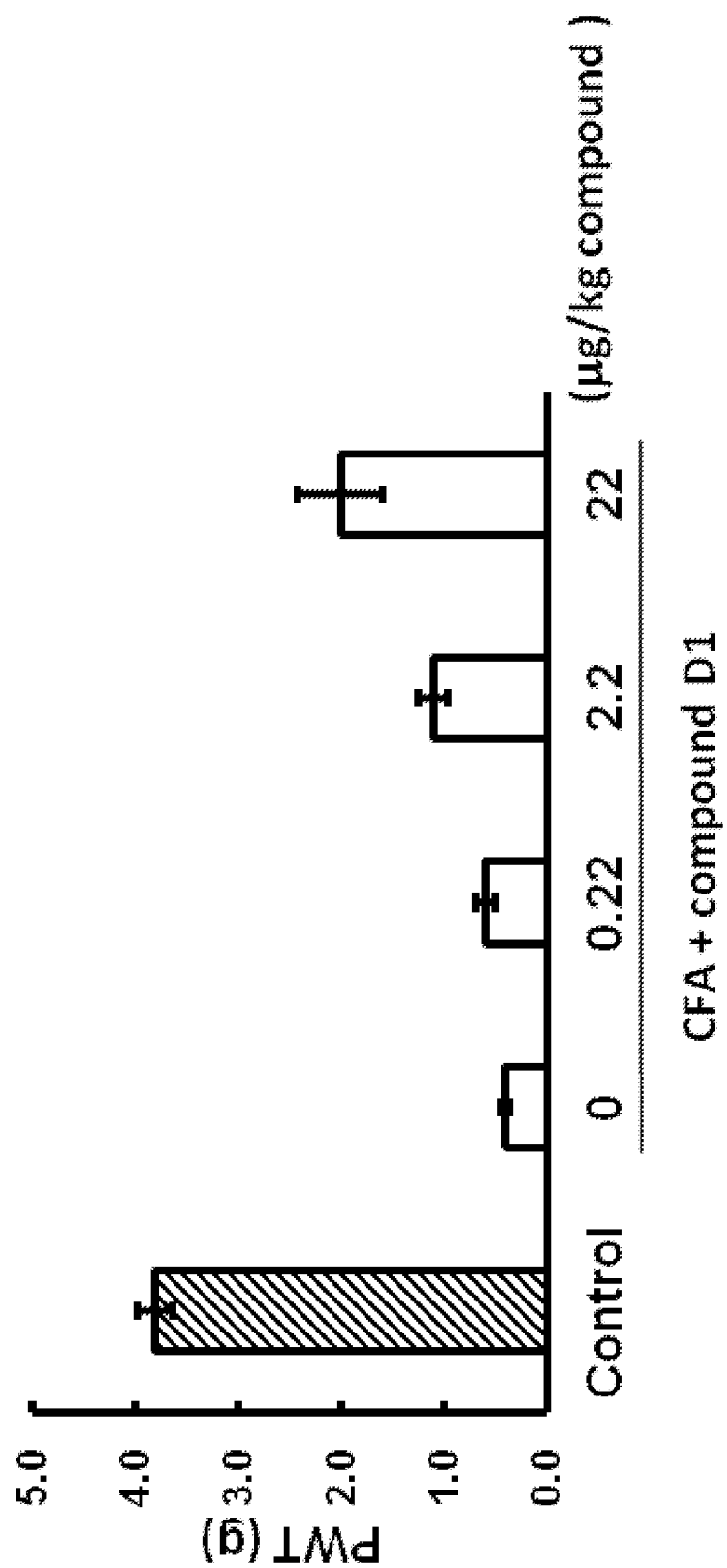
FIG. 4A shows the therapeutic dose effect of the compound D1 for alleviating chronic inflammatory pain induced by Complete Freund's Adjuvant.

As shown in FIG. 4A, the PWT of the mice injected with CFA decreased to 0.4±0.033 g. However, the PWT of the mice injected with 2.2 µg/kg of the compound D1 recovered to 1.1±0.15 g, and the PWT recovered to 2.0±0.411 g following a intraplantar injection of 22 µg/kg of the compound D1, which indicates that the dosage of the compound D1 was sufficient to ease the chronic inflammatory pain (compared with control PWT 3.8±0.171 g). The results show that the compound had the effect of alleviating inflammatory pain caused by CFA.

Figure 4B:
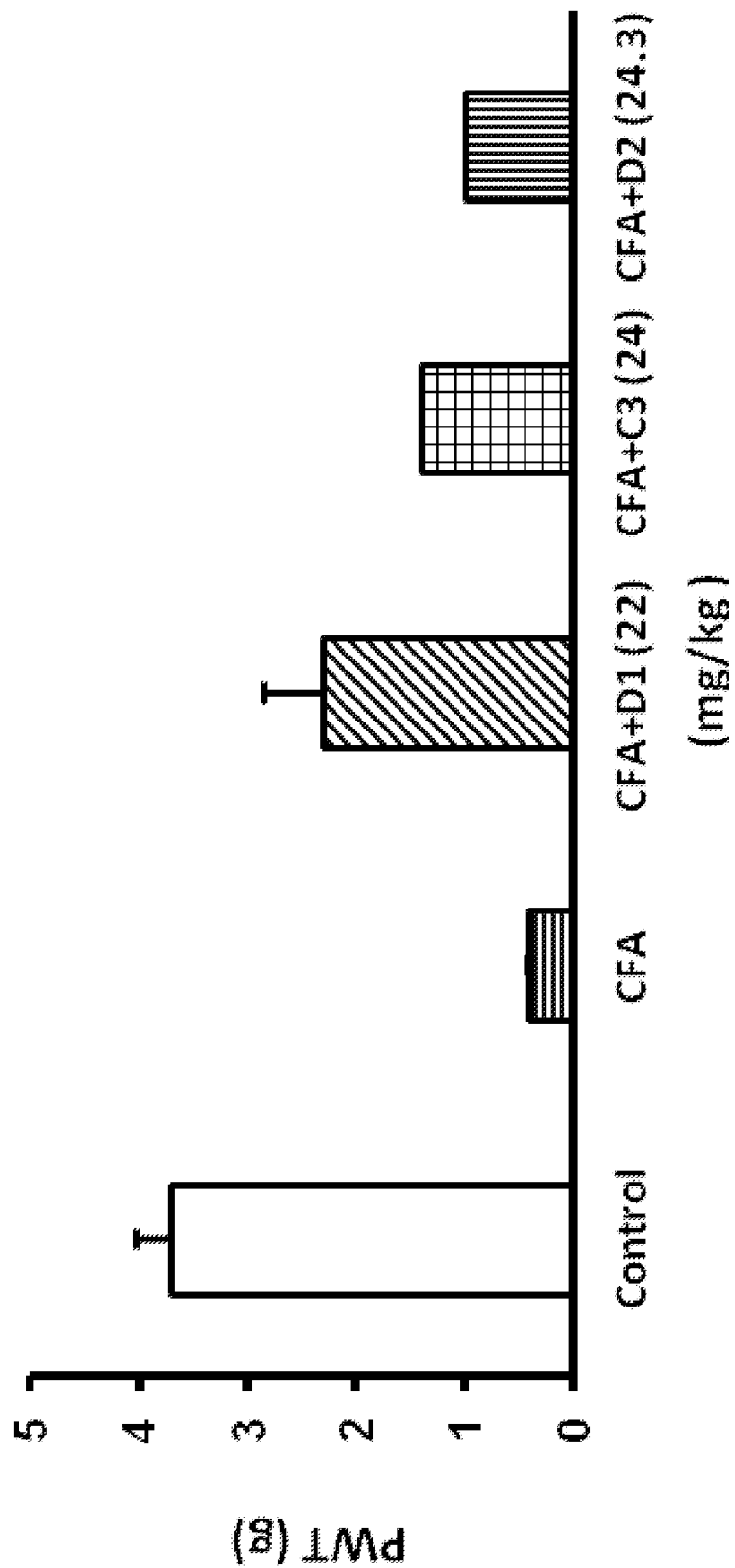
FIG. 4B shows the therapeutic effect of the compound D1, C3, D2 for alleviating chronic inflammatory pain induced by Complete Freund's Adjuvant.

As shown in FIG. 4B, the PWT of the mice injected with 22 µg/kg of the compound D1 recovered to 2.3 g (compared with control PWT 3.8±0.171 g), and the PWT recovered to 1.4 g or 1.0 g following an intraplantar injection of 24 µg/kg of the compound C3 or 24.3 µg/kg of the compound D2, respectively. The results show that the trend of the effective dosages of these compounds is D1<C3<D2.

In accordance with the results above, the naphtho[2,3-f] quinoxaline compound and its pharmaceutical composition actively alleviated pain in organisms and the results also show how to choose therapeutically effective amounts of the compound as well as different administration methods for specific subjects. The pain can be any types of pain including, but not limited to, neuropathic pain (such as the pain caused by diabetes), visceral pain, pain after surgery, pain caused by cancer or treatments of cancer, headache, muscle pain, and inflammatory pain caused by arthritis or irritable bowel syndrome.

The term excipients or "pharmaceutically acceptable carrier or excipients" and "bio-available carriers or excipients" mentioned above include any appropriate compounds known to be used for preparing the dosage form, such as a solvent, a dispersing agent, a coating, anti-bacterial or anti-fungal agents and preserving agents or delayed absorbents. Typically, carriers and excipients do not have any therapeutic effect. Each formulation is prepared by combining the derivatives disclosed in the present invention and pharmaceutically acceptable carriers or excipients that will not cause undesired effects, allergies or other inappropriate results when administered to an animal or human. Accordingly, the derivatives disclosed in the present invention in combination with pharmaceutically acceptable carriers or excipients are adaptable in clinical usage and in human patients. The term "therapeutically effective amount" mentioned herein, refers to an amount sufficient to ameliorate or prevent the medical symptom. The therapeutically effective amount also explains the dosage of the compound that is suitable for use. Unless otherwise stated in the specification, the "active compound" and "pharmaceutically active compound" mentioned herein are essentially the same, which refer to a substance that has a pharmaceutic, pharmacological, therapeutic or other effect.

The carrier may vary with each formulation, and the sterile injection composition can be dissolved or suspended in non-toxic intravenous injection diluents or solvents such as 1,3-butanediol. Among these carriers, an acceptable carrier may be mannitol or water. In addition, fixing oil, synthetic glycerol ester, and di-glycerol ester are commonly used solvents. Fatty acids such as oleic acid, olive oil, castor oil and glycerol ester derivatives thereof, especially the oxy-acetylated types, may serve as the oil for preparing the injection and as natural pharmaceutically acceptable oil. This oil solution or suspension may include long chain alcohol diluents or dispersing agents, carboxylate methyl cellulose (CMC) or an analogous dispersing agent. Other acceptable carriers are common surfactants such as Tween and Spans, another analogous emulsion, or a pharmaceutically acceptable solid, liquid or other bio-available enhancing agent used to develop a formulation that is used in the pharmaceutical industry.

The composition for oral administration may use any acceptable oral formulation, which includes capsules, tablets, pills, emulsions, aqueous suspensions, dispersing agents and solvents. The carrier is generally used in oral formulations. Taking a tablet as an example, the carrier may be lactose, corn starch and lubricant, and magnesium stearate is the basic additive. The diluents used in the capsule include lactose and dried corn starch. To prepare an aqueous suspension or an emulsion formulation, the active ingredient is suspended or dissolved in an oil interface in combination with the emulsion or the suspending agent, and an appropriate amount of sweetening agent, flavors or colorant is added as needed.

Using the animal model to evaluate the analgesic effect of the compound

Nociceptive Pain—the Acute Pain Induced by Acid Solution

25 μL of acid solution with a pH of 5.0 was injected into 8 to 12-week-old CD-1 mice in order to induce mechanical hyperalgesia. Mice injected with saline were the control group; the ones that were injected with compound only were compound group; the ones that were injected with only the acid solution were the acid group and those injected with both compound and the acid solution were the acid+compound group.

The above-mentioned 1 M of pH 5.0 solution was prepared by dissolving 1.952 g of 2-(N-morpholino)ethanesulfonic acid (MES) in 10 mL of sterilized secondary water. The pH of the solution was adjusted to 5.0 using 1N NaOH solution. Before injection, pH5.0 was diluted with saline into 10 mM.

2.2 μg/kg of the compound was administered to the mice by intraplantar injection about 5 minutes prior to the injection of the acid solution. An hour after the injection of the acid, the hypersensitivity of the mice to mechanical stimuli was measured using von Frey filaments (Touch-Test North Coast Medical, Inc., Margan Hill, Calif.). The mice were placed in transparent plastic chambers (10×8×10 cm) on a metal mesh floor at least 30 minutes per day for 2 days to acclimatize them to the testing room prior to the test. 60 minutes after the mice were administered with the compound, the mechanical hyperalgesia was assessed through the measurement of paw withdrawal frequencies by a sequential series of von Frey filaments of weights 0.6, 1.0, 1.4, 2.0 and 4.0 g applied perpendicularly to the plantar surface of the paw. The paw was briefly stimulated with force sufficient to slightly bend the filaments and a single trial consisted of repeated applications of the von Frey filaments five times, each application lasting for about 5 seconds. The occurrence of paw withdrawal resulting from the stimulation or removing the stimulation for each trial was quantified as a percentage response frequency for each filament. When the frequency was more than 50%, the weight of the von Frey filaments was determined as the paw withdrawal threshold (PWT). To make sure all the mice were under normal physical conditions, all housing conditions complied with general feeding standards, and the temperature and illumination were maintained in a suitable range.

Neuropathic Pain—Chronic Constriction Injury (CCI) of the Sciatic Nerve Induces Chronic Neuropathic Pain According to the method described by Bennett and Xie, Pain, 1988, 33, 87-107, 8 to 12-week-old CD-1 mice were subjected to the chronic constriction injury (CCI) of the sciatic nerve, which is an animal model inducing chronic neuropathic pain. To anesthetize the mice, each of the mice was injected with 240 mg/kg of 2,2,2-tribromoethanol (Avertin). Then three ligatures were loosely tied around the sciatic nerve of the mouse with chromic gut. The surgical procedure for the Sham (non ligation) control group was identical to that mentioned above except that the sciatic nerves were not ligated. A week after the mice in the experimental (CCI+compound) group had chronic constriction injury of sciatic nerves, the compound was intraplantarly, intrathecally, or intraperitoneally injected into the mice. 60 minutes after the injection, the mice were directly subjected to the hypersensitivity test to mechanical stimuli. The mice under the surgery treated with saline were the CCI group; the mice treated with gabapentin were the positive control (CCI+Gabapentin) group.

Inflammatory Pain—Chronic Inflammatory Pain Induced by CFA

To induce paw edema and chronic inflammatory pain, 25 µL of 50% Complete Freund's Adjuvant (CFA) in saline was intraplantarly injected into the right hind paw of the mouse. 5 minutes prior to the CFA injection, 0.22, 2.2 or 22 µg/kg of the compound was administered to the mouse by intraplantar injection. 60 minutes after the CFA injection, the hypersensitivity to mechanical stimuli was measured using von Frey filaments.

EMBODIMENTS

1. A method for alleviating a pain, the method comprises a step of administering to a subject suffering from the pain a pharmaceutical compound, wherein the pharmaceutical compound is a compound represented by one of Formula I and Formula II:

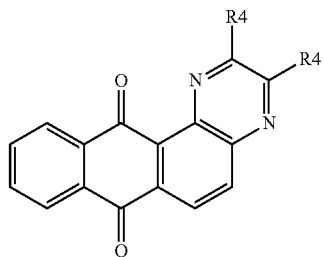

(I)

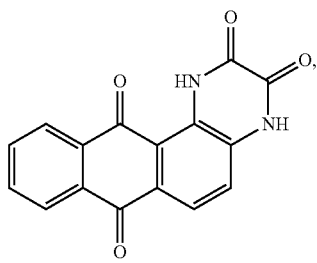

(II)

and R4 is one of hydrogen and methyl.

2. The method of Embodiment 1, wherein the pain is one of an acute pain and a chronic pain caused by one selected from a group consisting of an inflammation, an injury, and a neuropathy.

3. The method of any one of Embodiments 1-2, wherein the pain is one of an acute pain and a chronic pain caused by one of a cancer and a treatment of cancer.

4. A method for alleviating a pain, the method comprises a step of administering to a subject suffering from the pain a pharmaceutical composition including a therapeutically effective amount of compound, wherein the pharmaceutical compound is a compound represented by one of Formula I and Formula II, and R4 is one of hydrogen and methyl.

5. The method of Embodiment 4, wherein the pain is one of an acute pain and a chronic pain caused by one selected from a group consisting of an inflammation, an injury, and a neuropathy.

6. The method of any one of Embodiments 4-5, wherein the pain is one of an acute pain and a chronic pain caused by one of a cancer and a treatment of cancer.

7. A method for inhibiting an onset of an inflammatory pain comprises a step of administering to a subject suffering from the onset a pharmaceutical compound, wherein the pharmaceutical compound is a compound represented by one of Formula I and Formula II, and R4 is one of hydrogen and methyl.

8. The method of Embodiment 7, wherein the pharmaceutical compound is administered to the subject with a pharmaceutical excipient.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims that are to be accorded with the broadest interpretation so as to encompass all such modifications and similar structures.

What is claimed is:

1. A method for alleviating a pain selected from the group consisting of chronic inflammatory pain, nociceptive pain, and neuropathic pain, the method comprising a step of: administering to a subject suffering from the pain a pharmaceutical compound, wherein the pharmaceutical compound is a compound represented by one of Formula I and Formula II:

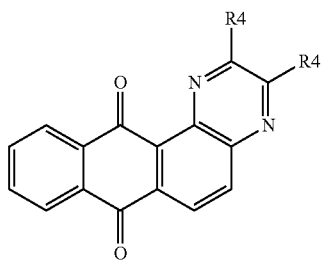

(I)

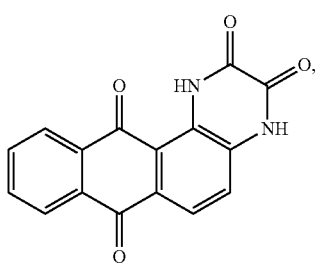

(II)

and R4 is one of hydrogen and methyl.

2. The method as claimed in claim 1, wherein the pain is the chronic inflammatory pain and is caused by a cancer caused by one of a cancer and a cancer treatment.

3. A method for alleviating a pain selected from the group consisting of chronic inflammatory pain, nociceptive pain, and neuropathic pain, the method comprising a step of: administering to a subject suffering from the pain a pharmaceutical composition including a therapeutically effective amount of compound, wherein the pharmaceutical compound is a compound represented by one of Formula I and Formula II:

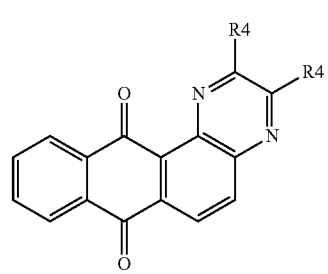
and R4 is one of hydrogen and methyl.
4. The method as claimed in claim 3, wherein the pain is the chronic inflammatory pain and is caused by a cancer caused by one of a cancer and a cancer treatment.
* * * * *